United States Patent [19]

Goldberg

[11] Patent Number: 5,378,637
[45] Date of Patent: Jan. 3, 1995

[54] METHOD FOR MEASURING HYALURONIC ACID

[75] Inventor: Ronald L. Goldberg, Verona, N.J.

[73] Assignee: Ciba Corning Diagnostics Corp., Medfield, Mass.

[21] Appl. No.: 115,926

[22] Filed: Sep. 1, 1993

Related U.S. Application Data

[63] Continuation of Ser. No. 521,788, May 10, 1990, abandoned, which is a continuation-in-part of Ser. No. 70,476, Jul. 7, 1987, abandoned.

[51] Int. Cl.$^6$ ............... G01N 33/566; G01N 33/567; G01N 33/53; A61K 37/12
[52] U.S. Cl. ............... 436/501; 436/503; 436/509; 436/518; 435/7.1; 435/7.8; 435/7.92; 435/7.94; 435/7.93; 435/967; 530/356; 530/357; 530/388.23
[58] Field of Search ............... 435/7.1, 7.8, 7.92, 435/7.94, 7.93, 820, 967; 436/506, 509, 501, 503, 518; 530/356, 357

[56] References Cited

U.S. PATENT DOCUMENTS

| | | | |
|---|---|---|---|
| 4,704,356 | 11/1987 | Thonar | 435/7 |
| 4,743,560 | 5/1988 | Campbell et al. | 436/501 |
| 4,826,776 | 5/1989 | Brandt et al. | 436/501 |
| 4,891,313 | 1/1990 | Berger et al. | 436/7 |

OTHER PUBLICATIONS

Thonar, et al., Arthritis and Rheumatism vol. 28 (12) pp. 1367-1376 (1985).
Bonnet, et al., Biochem. J. vol. 288 pp. 77-85 (1985).
Delpech, et al., Analytical Biochemistry vol. 149 pp. 555-565 (1985).
Tengblad, Biochem J. vol. 185 pp. 101-105 (1980).
Akiyama, et al., Ar. of Biochemistry and Biophysics vol. 252 (2) pp. 574-590 (1987).
Christner, J. D., et al., J. Biol. Chem. 254, 4624-4630 (1979).
Hascall, V. C., et al. "Proteoglycans: Isolation and Characterization" Methods in Enzymology, vol. 82, 769-785 (1982).
Keiser, Anal. Biochem. Feb. 1, 1987, 160 (2) pp. 462-467 abstract only.
J. Biol. Chem., 258(14), 258(14), 1983, B. Caterson et al.; abstract only.
Caterson et al., J. Biol. Chem. 258 (14) pp. 8848-8854 (1983).

Primary Examiner—Margaret Parr
Assistant Examiner—Bradley Lounsbury Sisson
Attorney, Agent, or Firm—Nicholas I. Slepchuk, Jr.; Judith A. Roesler; Arthur S. Morgenstern

[57] ABSTRACT

A method for measuring hyaluronic acid in a biological sample which comprises (a) coating a solid support with hyaluronic acid; (b) incubating the sample with cartilage proteoglycan; (c) exposing the incubated sample to the coated solid support; (d) then exposing the coated solid support to a keratan sulfate-reactive antibody; (e) determining the amount of antibody linked to keratan sulfate; and (f) correlating the amount of antibody linked to the keratan sulfate to the amount of hyaluronic acid in the sample.

6 Claims, 2 Drawing Sheets

METHOD FOR MEASURING HYALURONIC ACID

RELATED APPLICATIONS

This application is a continuation of U.S. patent application Ser. No. 07/521,788, filed May 10, 1990, now abandoned, which was a continuation-in-part of U.S. patent application Ser. No. 07/070,476, filed Jul. 7, 1987, now abandoned.

FIELD OF THE INVENTION

This invention relates to a method for measuring hyaluronic acid in biological fluids. More particularly, this invention relates to a method for measuring hyaluronic acid in biological fluids using cartilage proteoglycan and an antibody reactive with keratan sulfate.

BACKGROUND OF THE INVENTION

Changes in serum hyaluronic acid (hyaluronic acid is also known in the art as hyaluronate and hyaluronan) have been correlated with certain diseases. For example, an increase in serum hyaluronic acid has been found in patients having hepatic dysfunctions, such as cirrhosis. Additionally, there is a correlation between the increase in serum hyaluronic acid and cancer and rheumatoid arthritis. Methods for the detection and quantitation of hyaluronic acid in serum and other biological fluids are, therefore, desirable.

Cartilage proteoglycan core protein has a hyaluronic acid binding region which specifically and reversibly binds to hyaluronic acid. Keratan sulfate is a glycosaminoglycan covalently linked to the cartilage proteoglycan core protein in several areas and is concentrated in the keratan sulfate-rich region near the hyaluronic acid binding region.

Several radioassays have been disclosed for measuring the amount of hyaluronate in biological samples. For example, the Pharmacia HA Test 50 (Pharmacia Diagnostics AB, Uppsala, Sweden) is a radiometric assay for the determination of hyaluronic acid using $^{125}$I-labelled hyaluronic acid binding proteins from bovine cartilage. See also, A. Tengblad, "Quantitative Analysis of Hyaluronate in Nanogram Amounts" Biochem. J. 185, 101–105 (1980).

In Thonar et al, "Quantification of keratan Sulfate in Blood as a Marker of Cartilage Catabolism" Arthritis and Rheumatism 28(12), 1367–1376 (1985), there is described an enzyme-linked immunosorbent-inhibition assay (ELISA) using a monoclonal antibody specific for keratan sulfate to quantify keratan sulfate present as single chains in adult human serum.

In Delpech et al, "Immunoenzymeassay of the Hyaluronic-Hyaluronectin Interaction: Application to the Detection of Hyaluronic Acid in Serum of Normal Subjects and Cancer Patients" Anal Biochem 149, 555–565 (1985), the authors describe a method for investigating the binding of a hyaluronic acid-binding glycoprotein, hyaluronectin, extracted from the human brain, to hyaluronic acid using an enzyme-linked immunosorbent assay technique. This reference states the hyaluronectin is a protein component from the human brain which combines in vitro with hyaluronic acid but not with other glycosaminoglycans.

Prior to the present invention, there was no non-isotopic method for measuring the amount of hyaluronate in biological samples using cartilage proteoglycan.

SUMMARY OF THE INVENTION

This invention relates to a method for measuring hyaluronic acid in a biological sample which comprises:
 (a) linking hyaluronic acid to a solid support to produce a coated solid support;
 (b) incubating the sample with cartilage proteoglycan;
 (c) exposing the incubated sample of step (b) to the coated solid support of step (a) to bind free cartilage proteoglycan to the linked hyaluronic acid on the coated solid support;
 (d) exposing the product of step (c) to a keratan sulfate-reacting antibody to link the antibody to the keratan sulfate of the cartilage proteoglycan bound to the linked hyaluronic acid on the coated solid support;
 (e) determining the amount of antibody linked to the keratan sulfate; and
 (f) correlating the amount of antibody linked to the keratan sulfate to the amount of hyaluronic acid in the sample.

DESCRIPTION OF THE INVENTION

Figure 1:
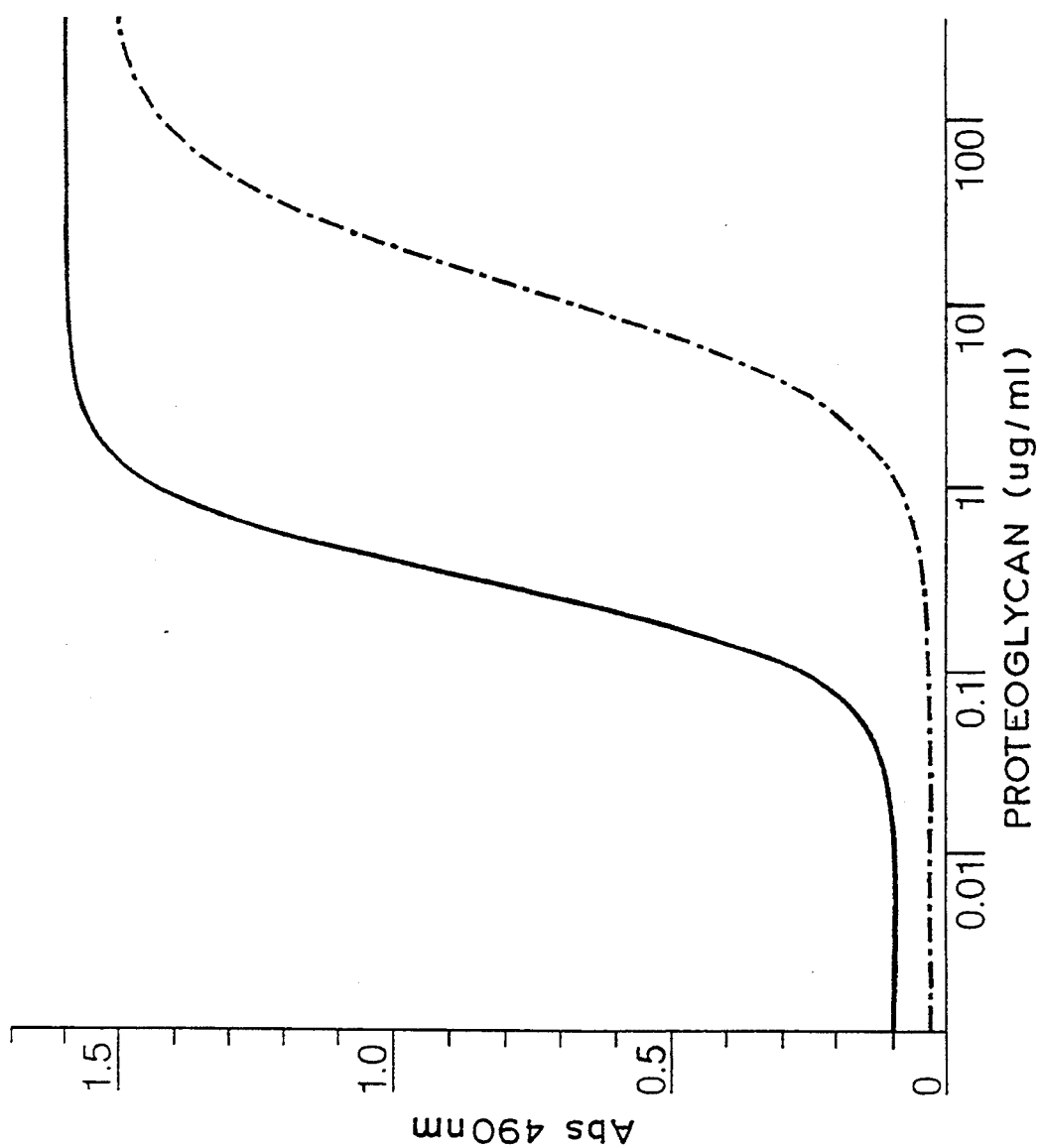
FIG. 1 is a graph showing the relative amount of cartilage proteoglycan bound to plates coated with hyaluronate, both in the presence and absence of additional hyaluronate.

In a preferred embodiment of the method of this invention, microtiter plates are coated with hyaluronic acid. The amount of hyaluronic acid used to coat the microtiter plates can vary over a wide range, but it is usually in the concentration range of about 20 ug to about 40 ug per well, in 200 ul of buffer (at a preferred pH of 9–9.5) for a typical Nunc 96-well plate. The hyaluronic acid can be derived from any convenient source. One such source is human umbilical cord (Sigma, Grade III).

In the inhibition step, in separate "dummy" (i.e., no linked hyaluronate) plates, aliquots of a solution containing cartilage proteoglycan are incubated with various known concentrations of hyaluronic acid and with unknown samples of blood plasma or serum for a period of time sufficient to permit substantially complete reaction of the proteoglycan with the hyaluronic acid. Then, equal amounts of the incubation mixtures are applied to the hyaluronate-coated plates and incubated for a period of time sufficient for free proteoglycan, which was not prereacted (inhibited) with the hyaluronate in solution, to react with the hyaluronate coated on the plates. The incubation conditions can vary within wide limits, but an incubation time of 16 to 24 hours and an incubation temperature of 4° C. is satisfactory, although incubation times of as little as 1 to 2 hours at room temperature are also operable. The plates are washed thoroughly to remove all proteoglycan, hyaluronate and proteoglycan-hyaluronate complex that is not bound to the plates. It has been found that a particularly effective buffering system for aggregation of proteoglycan and hyaluronic acid is a mixture of 0.5% to 1% bovine serum albumin and 0.05% Tween.

Next, aliquots of a solution containing a keratan sulfate-reactive antibody (preferably a monoclonal antibody) are applied to the plates and incubated for a period of time sufficient to permit substantially complete reaction of the antibody with the keratan sulfate associated with the proteoglycan bound to the hyaluronate on the plates. Monoclonal antibodies specifically reactive with keratan sulfate are known in the art. See, e.g., Bruce Caterson, J. Biol. Chem. 258, 8848–8854 (1983).

As a means of visualizing the amount of antibody that is bound to the plate, the plate is exposed to an excess of a second antibody that reacts with the anti-keratan sulfate antibody and which is appropriately labelled with an enzyme or other non-isotopic marker. For example, if the first antibody is an anti-keratan sulfate monoclonal mouse antibody, the enzyme label may be linked to anti-mouse immunoglobulin. A preferred means of labelling the second antibody is by linkage to an enzyme, such as peroxidase, which catalyzes a colorimetric reaction by which its presence is reported. An example of a suitable peroxidase catalized reporter reaction is described in the *Journal of Biological Chemistry* 257: 14173–14180, 1982. Other enzymatic reporter systems may be substituted for the peroxidase reporter system as a means for visualizing keratan sulfate-bound antibodies. A suitable enzyme-linked anti-keratan sulfate antibody is a peroxidase-conjugated anti-mouse IgG antibody.

Alternatively, a reporter system can be coupled directly to the cartilage proteoglycan by chemically reacting the reporter substance with streptavidin, using known techniques. Suitable reporter substances that can be modified in this way include enzymatic, fluorescent and chemiluminescent compounds. The cartilage proteoglycan is modified by biotinylation, thus permitting direct binding of the reporter substance to the proteoglycan. This embodiment has the advantage of eliminating the requirement of a first and second antibody in the assay.

The absorbences of the plates can then be read with an MR600 Microplate Reader (Dynatech, Alexandria, Va.), for example, either directly or with the aid of a computer.

In this preferred assay system, the more hyaluronic acid that is present in the sample, the less color that develops. Although the degree of color development is a function of hyaluronic acid concentration in the sample, it is a log linear relationship. Accordingly, it is necessary to prepare a standard curve from known hyaluronic acid standard concentrations against which the color development in an unknown specimen can be compared. The standard curve for this assay is generally log linear over only a limited hyaluronic acid concentration range, and in order that the level of hyaluronic acid in an unknown sample can be read with accuracy from a standard curve, it is preferred to perform the assay on serial dilutions of each sample to assure that one or more of the serial dilutions of each sample assay fall within the log linear range of the standard curve.

An ELISA assay system that is constructed based on this invention preferably contains from about 1 ng to about 100 ng of soluble hyaluronic acid, and from about 50 ng to about 500 ng of cartilage proteoglycan per 10 to 100 ul of serum sample which is analyzed. Amounts of anti-keratan sulfate antibody employed range from 1:2,000 to 1:20,000 dilution of ascites fluid. Amounts of enzyme-linked antibody employed range from 1:500 to 1:2,000 dilution. A total volume of 200 to 250 ul per well is the preferred volume.

While this invention has been described in terms of certain preferred embodiments, modifications obvious to one skilled in the art may be made without departing from the scope of the invention. For example, an isotopic fluorescent or chemiluminescent label on the second antibody or on the keratan sulfate-reactive antibody can be used to determine the amount of keratan sulfate-reactive antibody linked to the keratan sulfate of the proteoglycan bound to the hyaluronic acid linked to the coated solid support. The method of this invention can be used to measure hyaluronic acid in the biological fluids of humans and lower animals as well.

The following example is provided to further illustrate a typical embodiment of this invention, and should not be considered to limit the invention or the scope of the appended claims.

EXAMPLE

In this Example, absorbences were read with a Dynatech MR600 reader (Alexandria, Va.). Data capture and processing was done with an Apple IIe computer using the "650 READ" program (Dynatech). Graphics were drawn with the Hewlett-Packard 7470A plotter (San Diego, Calif.) using first "ALLFIT" [Biomedical computing Technology Information Center, (BCTIC), Vanderbilt Medical Center, Nashville, Tenn.] curve fitting program followed by "SCIENTIFIC PLOTTER" (Interactive Microware, State College, Pa.). Plates, 96 well, (Nunc-Immuno plates IF, Roskilde, Denmark) were shaken in a Dynatech Micro-Shaker II placed in a precision oven at 37° C. Plates were washed with a Dynatech Dynawasher II. Solution dispensing was done with 12-channel Titertek (Flow Lab., McLean, Va.) pipets, 5–50 and 50–200 ul, Eppendorf (Brinkman Institute, Westbury, N.Y.) pipets with Combitips, and Gilson (Rainin Institute, Woburn, Mass.) pipetmen. Chromatography columns were from Pharmacia (Uppsala, Sweden) C-26.

Phosphate-buffered saline (PBS), 10X and 1X, were from GIBCO (Charin Falls, Ohio). Bovine serum albumin (BSA, RIA grade), Tween 20, and O-phenylenediamine were from Sigma (St. Louis, Mo.). Testicular hyaluronidase (bovine testes) and hyaluronate, Grades I (human umbilical cord) III (human umbilical cord), and IV (bovine vitreous humor), were from Sigma. Peroxidase coupled to anti-mouse IgG, H+L (rb), was from Miles Laboratories (Naperville, Ill.). Recombinant human interleukin 1a was from Biogen batch No. RN81885113, Sephadex G-50 resin was from Pharmacia (Piscataway, N.J.). Spectrograde methanol was from Baker (Phillipsburg, N.J.). The proteoglycan D1 and the monoclonal antibody 4A4 were obtained form Dr. Eugene Thonar (Rush Presbyterian-St. Lukes Medical School, Chicago, Ill.). Proteoglycan monomer and an antibody to keratan sulfate can be purchased from ICN ImmunoBiologicals (Lisle, Ill.).

Hyaluronate (Grade III) was dissolved in water at a concentration of 0.2 mg/ml then diluted to 0.1 mg/ml with 0.2M sodium carbonate, pH 9.2. To each well in the Nunc 96-well plate 0.2 ml of this solution was added. After an overnight incubation at 4° C. the plates were incubated with 5% BSA-PBS for 6 h then washed twice with PBS containing 0.02% sodium azide and stored sealed and refrigerated in this buffer. The plates were washed twice with 0.05% TWEEN 20 surfactant/PBS immediately before use. The plate coating was stable for 6 months of storage.

Dummy plates, used for preincubation of samples and proteoglycan, were first incubated with 1% BSA-PBS to block binding of proteoglycans to the plate.

Proteoglycan (D1) was dissolved in 0.1% BSA-PBS at 0.4 mg/ml and stored frozen in 1-ml portions. Hyaluronate (Grade I) was dissolved in water, 10X PBS was added (1:10 v/v) to make a final solution of 0.2 mg hyaluronate/ml PBS based upon uronic acid content, and then the hyaluronate solution was stored frozen in 1-ml portions. Proteoglycan and hyaluronate stock solutions were thawed at 37° C. just before use and diluted 1:10 (v/v) with 1% BSA-PBS.

The standards and unknown were added first to a dummy plate (a non-hyaluronate-coated Nunc plate) or directly to a hyaluronate-coated plate in a total volume of 0.1 ml. Diluting buffer was 1% BSA-PBS. Proteoglycan (0.04 mg/ml) was then added in a volume of 0.01 ml followed by 0.02 ml of a solution of 10X PBS, 5% BSA, 0.5% TWEEN 20 surfactant, and 0.05% azide. PBS-0.1% BSA was added to make the total volume 0.2 ml. After a 24-h incubation at 4° C., samples in dummy plates were transferred to coated plates for another 24-h incubation at 4° C. If samples were added directly to coated plates, they were incubated for either 24 or 48 h.

The plates were washed five times using the Dynawasher with 0.05% TWEEN 20 surfactant/PBS buffer. The monoclonal antibody (4A4), which recognizes an epitope on the keratan sulfate of the proteoglycans, was diluted to 1:2000 or 1:4000 with PBS, 0.5% BSA, 0.05% TWEEN 20 surfactant and 0.2% ml added to each well. The plate was incubated at 37° C. with shaking for 1 h. The plate was washed and then incubated with peroxidase-conjugated anti-mouse IgG antibody, diluted 1:500 or 1:1000 with PBS, 0.5%, BSA, 0.05% TWEEN 20 surfactant for 1 h at 37° C. with shaking. The plate was washed and then incubated with 0.2 ml of freshly prepared substrate for 30–120 min. at room temperature. The substrate, o-phenylenediamine, was dissolved in methanol at 10 mg/ml, and then diluted to 0.1 mg/ml with water, followed by the addition of 3% hydrogen peroxide (1:1000 v/v). Color development was stopped by the addition of 0.05 ml of 50% sulfuric acid.

The plates were read in a Dynatech reader at 490 nm. The "650 READ" program was used to collect the data. For determining the best fit curve, a curve fitting program "ALLFIT" program was used. This program fits a sigmoid curve to the data. The fit parameters are estimated with error of estimate. Four parameters are fit to the following equation:

$$Y = ([A-D]/[1+\{X/C\}\wedge B]) + D,$$

where Y is the absorption at 490 nm and X is the concentration of hyaluronate; A is the maximum absorption (no inhibition), and D is the minimum absorption (maximum inhibition); B is the slope in the linear portion, and C is the concentration at the 50% value ($IC_{50}$).

For graphical analysis "SCIENTIFIC PLOTTER" was used with the modification for the Hewlett-Packard plotter. A subroutine using the above equation was used to draw the sigmoid curve.

Concentrations of the proteoglycan (D1) were varied as shown in FIG. 1, and the relative amount bound to the plates determined by the color change observed. Plates were coated with either 100 ug/ml of hyaluronate or BSA only (not shown in figure). When BSA only was used, no color change was observed at 200 ug/ml of concentration of proteoglycan. Various concentrations of proteoglycan were added either without (solid curve) or with (dashed curve) 20 ug/ml of hyaluronate. The $EC_{50}$ obtained was 0.3 ug/ml in the absence of excess hyaluronate (solid curve). When an excess of hyaluronate was incubated in the wells with the proteoglycan, the curve shifted to the right to give an $EC_{50}$ of 10 ug/ml (dashed curve). This shift illustrates that proteoglycan in this assay is analogous to the first antibody in a conventional inhibition ELISA, and that the procedure can be used to quantitate the amount of aggregatable proteoglycan.

Figure 2:
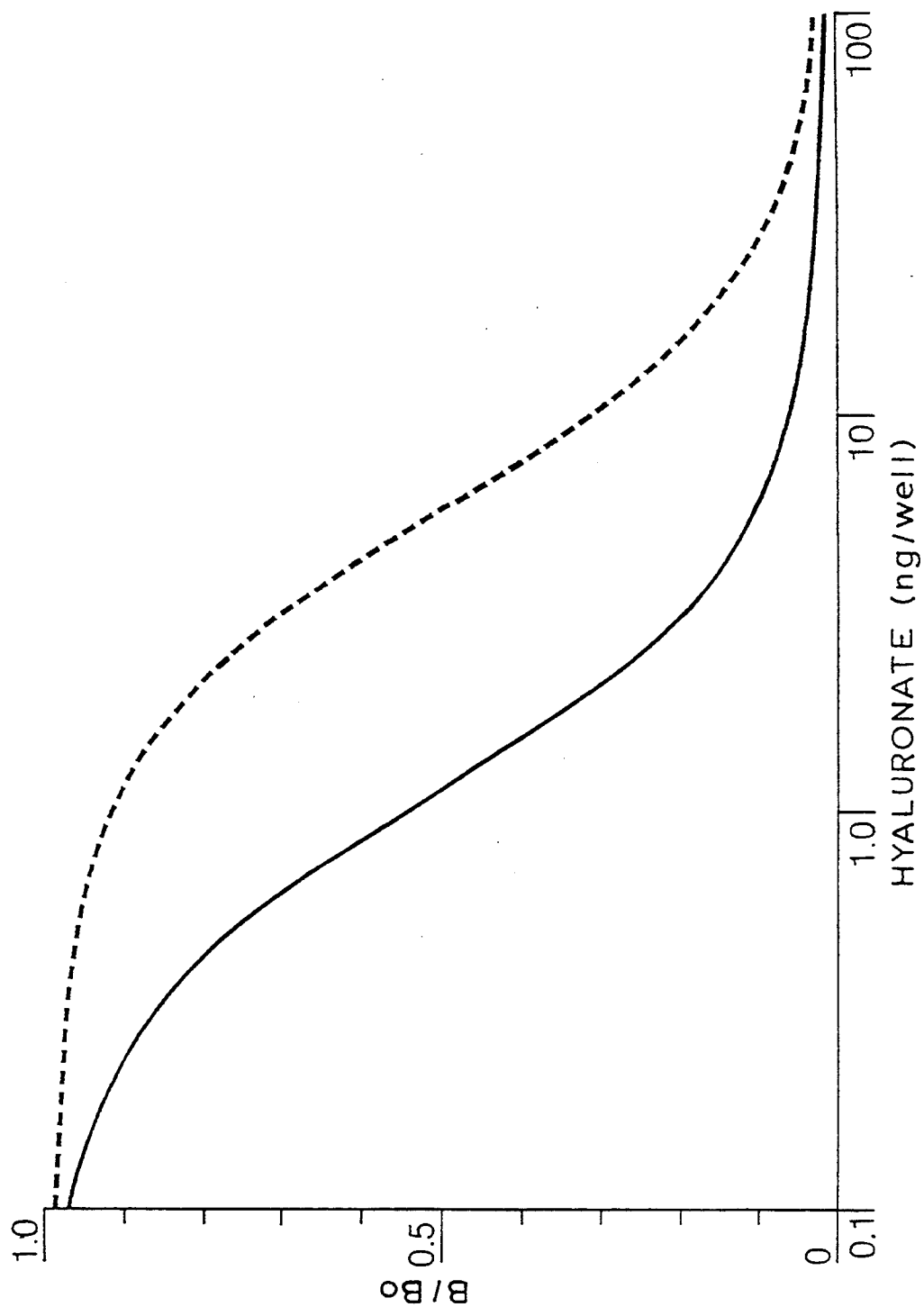
FIG. 2 is a graph showing the relative amount of cartilage proteoglycan bound to plates containing various amounts of hyaluronate, both with and without preincubation of the cartilage proteoglycan with additional hyaluronate.

The effect of preincubating the hyaluronate with 2 ug/ml of proteoglycan on the sensitivity of the ELISA (preincubation is generally believed to increase the sensitivity of an ELISA) is shown in FIG. 2. In FIG. 2, B is the amount of antibody bound to keratan sulfate in the presence of hyaluronate in a well, and $B_0$ is the amount of antibody bound to keratan sulfate in the absence of hyaluronte in a well. The hyaluronate and cartilage proteoglycan were preincubated for 24 hours in a dummy (non-coated) plate, and then transferred to a hyaluronate-coated plate for another 24 hours (solid line). This compares to direct addition of sample to coated plate with 48 hours of incubation (dashed line). The inhibition curve shifted to the left (more sensitive) with the preincubated samples, and there was a five-fold increase in sensitivity ($IC_{50}$ is 5 times lower).

What is claimed is:

1. A method for measuring hyaluronic acid in a biological sample comprising:
   (a) coating hyaluronic acid to a solid support to produce a hyaluronic acid coated solid support;
   (b) mixing the biological sample with cartilage proteoglycan, said cartilage proteoglycan having bound thereto keratan sulfate;
   (c) exposing the mixture of Step (b) to the solid support of Step (a) to bind said proteoglycan to the hyaluronic acid on the solid support to produce a detectable product;
   (d) exposing the product of Step (c) to a keratan sulfate specific antibody to bind to the keratan sulfate of the proteoglycan bound to the solid support;
   (e) detecting the amount of said keratan specific antibody bound to the keratan sulfate in Step (d); and
   (f) correlating the amount of said antibody detected in Step (e) to the hyaluronic acid in the biological sample,
   wherein prior to Step (b) said cartilage proteoglycan is preincubated with a known amount of unbound hyaluronic acid and wherein said cartilage proteoglycan and said unbound hyaluronic acid are contacted with a solution comprising bovine serum albumin and polyoxyethylene sorbitan monolaurate.

2. A method according to claim 1 wherein said cartilage proteoglycan is present in an amount ranging from about 50 ng/0.2 ml total volume to about 500 ng/0.2 ml total volume.

3. A method for measuring hyaluronic acid in a sample comprising:
   (a) coating hyaluronic acid to a solid support to produce a hyaluronic acid coated solid support;
   (b) mixing the sample with labelled cartilage proteoglycan;

(c) exposing the mixture of Step (b) to the solid support of Step (a) to bind said labelled proteoglycan to the hyaluronic acid on the solid support to produce a detectable product;

(d) determining the amount of product of Step (c) by detecting the labelled proteoglycan;

(e) correlating the amount of product in Step (d) to the amount of hyaluronic acid in the sample; and (f) generating a standard curve for known amounts of hyaluronic acid by performing steps (a) through (e) on samples having known concentrations of hyaluronic acid and using the standard curve to convert the detected amount of product into a corresponding value for hyaluronic acid contained in the test sample, wherein prior to Step (b) said cartilage proteoglycan is preincubated with a known amount of unbound hyaluronic acid and wherein said cartilage proteoglycan and said unbound hyaluronic acid are contacted with a solution comprising bovine serum albumin and polyoxyethylene sorbitan monolaurate.

4. A method according to claim 3 wherein said cartilage proteoglycan is present in an amount ranging from about 50 ng/0.2 ml total volume to about 500 ng/0.2 ml total volume.

5. A method for measuring hyaluronic acid in a biological sample comprising:

(a) coating hyaluronic acid to a solid support to produce a hyaluronic acid coated solid support;

(b) mixing the biological sample with a first solution comprising bovine serum albumin and polyoxyethylene sorbitan monolaurate, cartilage proteoglycan and hyaluronic acid, said cartilage proteoglycan having bound thereto keratan sulfate;

(c) exposing the mixture of Step (b) to the solid support of Step (a) to bind said proteoglycan to the hyaluronic acid on the solid support to produce a detectable product;

(d) separating said detectable product from unreacted reagents;

(e) exposing said separated detectable product of Step (d) to a keratan sulfate specific monoclonal antibody to bind to the keratan sulfate of the proteoglycan bound to the solid support;

(f) detecting the amount of said keratan specific antibody bound to the keratan sulfate in Step (e); and (g) correlating the amount of said antibody detected in step (f) to the hyaluronic acid in the biological sample.

6. A method according to claim 5 wherein said cartilage proteoglycan is present in Step (b) in an amount range from about 50 ng/0.2 ml total volume to about 500 ng/0.2 ml total volume.

* * * * *